US009869645B2

(12) United States Patent
Stuke et al.

(10) Patent No.: US 9,869,645 B2
(45) Date of Patent: Jan. 16, 2018

(54) SYSTEM FOR NON-DESTRUCTIVE TESTING AND METHOD FOR PROCESSING DATA GENERATED THEREIN

(75) Inventors: Ingo Stuke, Reinfeld (DE); Til Florian Guenzler, Lingen (DE); Michael Wuestenbecker, Lutjensee (DE); Andreas Beyer, Hamburg (DE)

(73) Assignee: General Electric Company, Schenectady, NY (US)

( * ) Notice: Subject to any disclaimer, the term of this patent is extended or adjusted under 35 U.S.C. 154(b) by 900 days.

(21) Appl. No.: 13/116,930

(22) Filed: May 26, 2011

(65) Prior Publication Data

US 2012/0303309 A1    Nov. 29, 2012

(51) Int. Cl.
*G06F 19/00* (2011.01)
*G01N 23/04* (2006.01)
*G06T 7/00* (2017.01)

(52) U.S. Cl.
CPC ..... *G01N 23/046* (2013.01); *G01N 2223/419* (2013.01); *G06T 7/0004* (2013.01); *G06T 2207/30164* (2013.01)

(58) Field of Classification Search
CPC .......... G01N 23/04; G01N 23/046; G01N 2223/419; G06T 2207/30164; G06T 2207/10081; G06T 7/0004
USPC ........................................................ 702/113
See application file for complete search history.

(56) References Cited

U.S. PATENT DOCUMENTS

| 4,896,278 | A | 1/1990 | Grove |
| 5,689,332 | A | 11/1997 | Ellingson et al. |
| 6,341,153 | B1 | 1/2002 | Rivera et al. |
| 6,765,570 | B1* | 7/2004 | Cheung .................. G06T 17/05 345/420 |
| 2005/0008213 | A1* | 1/2005 | Shankarappa et al. ....... 382/141 |
| 2007/0208234 | A1* | 9/2007 | Bhandarkar ........... A61B 19/52 600/300 |
| 2007/0217672 | A1* | 9/2007 | Shannon ............... G06T 7/0006 382/152 |

(Continued)

FOREIGN PATENT DOCUMENTS

WO    WO-2005095932    10/2005

OTHER PUBLICATIONS

Flisch et al. Industrial Computed Tomography in Reverse Engineering Applications, 1999, pp. 45-54.*

(Continued)

*Primary Examiner* — John Breene
*Assistant Examiner* — Mohammad Islam
(74) *Attorney, Agent, or Firm* — Barclay Damon LLP

(57) ABSTRACT

Systems and methods are described that reduce the amount of data that is transferred among the components of the system. In one embodiment, the testing system comprises a scanner device such as a computed-tomography (CT) scanner that generates a volumetric representation of a part-under-inspection. The testing system is further configured to identify a region of interest in the volumetric representation, wherein the region of interest may correspond to an area of the part-under-inspection where a defect or flaw may form. The testing system may further format the data of the volumetric representation so the resulting formatted volumetric representation comprises less data than the original volumetric representation.

18 Claims, 5 Drawing Sheets

(56) References Cited

U.S. PATENT DOCUMENTS

| | | | |
|---|---|---|---|
| 2008/0020350 A1* | 1/2008 | Matov | G06T 17/20 433/213 |
| 2008/0219532 A1* | 9/2008 | Hopkins | A61B 6/5258 382/131 |
| 2008/0247635 A1* | 10/2008 | Davis | G06T 19/00 382/152 |
| 2008/0247636 A1* | 10/2008 | Davis | G06T 19/00 382/152 |
| 2009/0169119 A1* | 7/2009 | Wegener | H04N 19/124 382/232 |
| 2009/0226063 A1* | 9/2009 | Rangwala et al. | 382/128 |
| 2009/0238432 A1* | 9/2009 | Can | G06T 7/001 382/132 |
| 2009/0307628 A1* | 12/2009 | Metala | G06T 7/0006 715/782 |
| 2011/0029114 A1* | 2/2011 | Rose | G06F 17/50 700/97 |
| 2011/0182495 A1* | 7/2011 | Sun | G06T 7/0004 382/141 |
| 2011/0222754 A1* | 9/2011 | Zhao | G06T 7/0004 382/141 |
| 2012/0257713 A1* | 10/2012 | Noel | G01N 23/046 378/19 |
| 2013/0094740 A1* | 4/2013 | Vandenberghe | A61B 6/14 382/131 |
| 2013/0226534 A1* | 8/2013 | Fisker | G06F 17/50 703/1 |

OTHER PUBLICATIONS

A Novel Feature-Based Tracking Approach to the Detection, Localization, and 3-D reconstruction of internal defects in hardwood logs using computer tomography, Suchendra M. Bhandarkar et al., Published online: Aug. 18, 2006, 21 pages.

\* cited by examiner

US 9,869,645 B2

SYSTEM FOR NON-DESTRUCTIVE TESTING AND METHOD FOR PROCESSING DATA GENERATED THEREIN

BACKGROUND OF THE INVENTION

The subject matter disclosed herein relates to non-destructive testing and, more particularly, to systems and methods useful for defect detection in manufacturing environments.

Non-destructive testing can be done by testing systems that may deploy equipment to inspect of the interior of parts. This equipment includes computed-tomography (CT) scanners, ultrasonic scanners, X-ray scanners, and magnetic resonance inspection (MRI) scanners. Many of these scanners generate images of the part. These images permit visual inspection of the part without the need to disrupt the structural integrity of the part-under-inspection. In many cases, the images or related output of the scanners comprise a large amount of data.

Many testing systems preserve all of the data that correspond to the images, which can slow certain functions that require transfer of the data to and from other locations such as to store, to archive, and to retrieve the data from remote locations where data storage facilities are found. Moreover, the large amount of data that the testing systems maintain is often unnecessary because the subject of the inspection (e.g., the defect and/or the flaw) is oftentimes located only in small portions of the part-under-inspection.

The discussion above is merely provided for general background information and is not intended to be used as an aid in determining the scope of the claimed subject matter.

BRIEF DESCRIPTION OF THE INVENTION

The discussion below highlights embodiments of a system and a method to reduce the amount of data that must be transferred to perform functions associated with data transfer.

In one embodiment, a testing system comprises a scanner device and a control unit coupled to the scanner device. The control unit is operatively configured to instruct the scanner device to generate a volumetric representation of a part-under-inspection, to locate a defect in the volumetric representation, and to generate a formatted volumetric representation having less data than the volumetric representation.

In another embodiment, a method for reducing data in a non-destructive testing system comprises steps for performing a scan of a part-under-inspection, generating a volumetric representation from the scan, and identifying a defect in the volumetric representation. The method also comprises steps for establishing a region of interest around the defect and generating a formatted volumetric representation having less data than the volumetric representation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
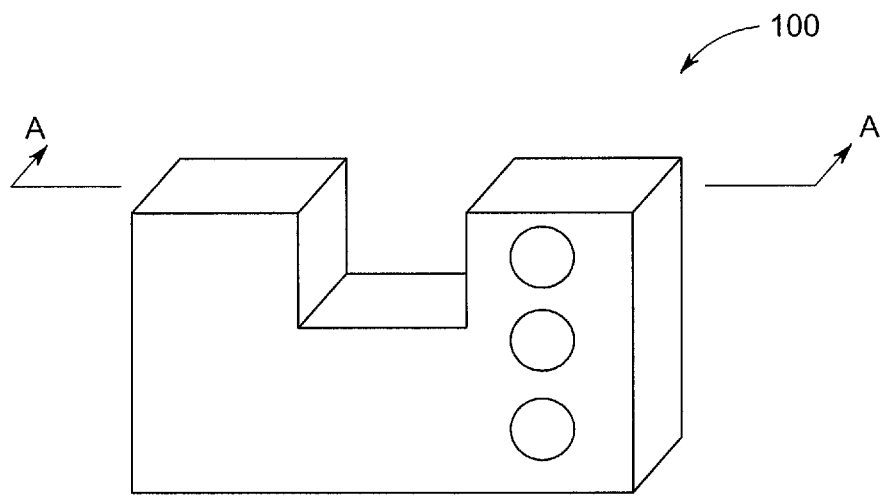
FIG. 1 depicts an example of a part-under-inspection.

FIG. 1 depicts an example of a part-under-inspection 100 (or "part 100") that can result from a variety of manufacturing processes (e.g., casting, forging, molding, welding, machining, forming, etc). The part 100 may be subject to non-destructive testing techniques that may utilize various imaging technologies including computed-tomography (CT) scanners, X-ray imagers, magnetic resonance imagers ("MRI"), ultrasonic scanners, and the like. Such technology can generate a volumetric representation of the part 100 that shows the interior of the part 100 normally hidden from view. This feature permits the end user to perform certain inspection and analysis tasks without the need to sacrifice the structural integrity of the part 100.

Figure 2:
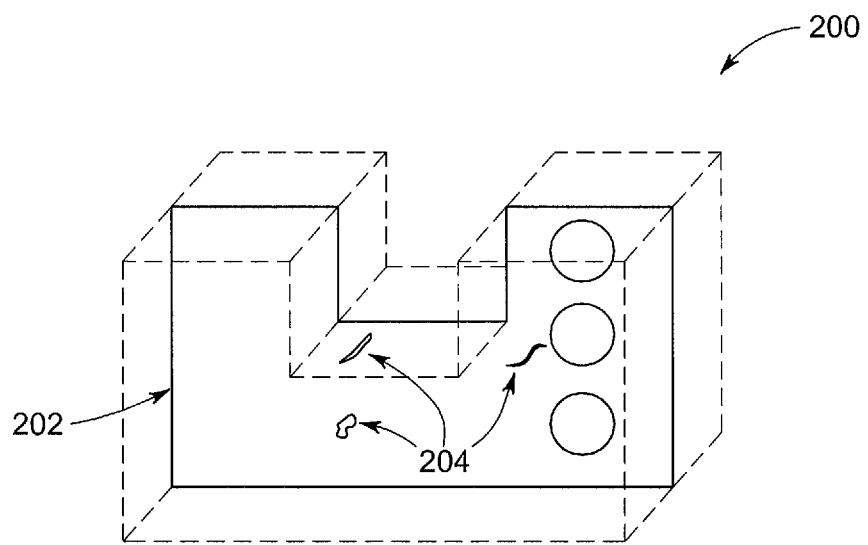
FIG. 2 depicts an example of a volumetric representation of a part-under-inspection such as the part-under-inspection of FIG. 1.

FIG. 2 illustrates an example of a volumetric representation 200 of the part 100 (FIG. 1) and, more particularly, the volumetric representation 200 includes an interior area 202, shown here in cross-section taken along line A-A of FIG. 1. The interior area 202 includes defects 204, which the end user might not readily observe because the defects 204 are found below the surface of the part 100. Examples of defects 204 include material defects, e.g., occlusions and porosity, and manufacturing defects that the manufacturing process and/or the application in which the part is implemented may cause. Manufacturing defects include fracture, creep, and corrosion, all of which may be hidden from view and may cause or generate failures in the part 100. Moreover, while the discussion below may focus on defects internal to the part, the systems and methods below are likewise applicable to those defects that appear on the surface of the part 100.

In one embodiment, the volumetric representation 200 may represent anywhere from several hundred megabits (MB) to several thousand MB or gigabits and even terabits of data. This data is often stored, archived, or otherwise maintained and/or provided with a unique identifier such as a serial number to make the volumetric representation 200 available, e.g., for further inspection, analysis, and comparison. In one implementation, the data respecting the volumetric representation 200 may be transferred to and from devices that are located remote from one another such as from a testing system to a data storage device (e.g., a server), and vice versa.

The present disclosure describes subject matter that improves this transfer by selectively reducing the amount of data associated with the volumetric representation 200. The data respecting the volumetric representation 200 is manipulated and, in one embodiment, the technical effect of such manipulation (and embodiments of the systems and methods) is to detect and to retain the data that is representative of and/or proximate defects 204. The data not detecting and/or associating with a defect may be discarded or otherwise formatted to reduce the overall amount of data associated with the volumetric representation 200.

Figure 3:
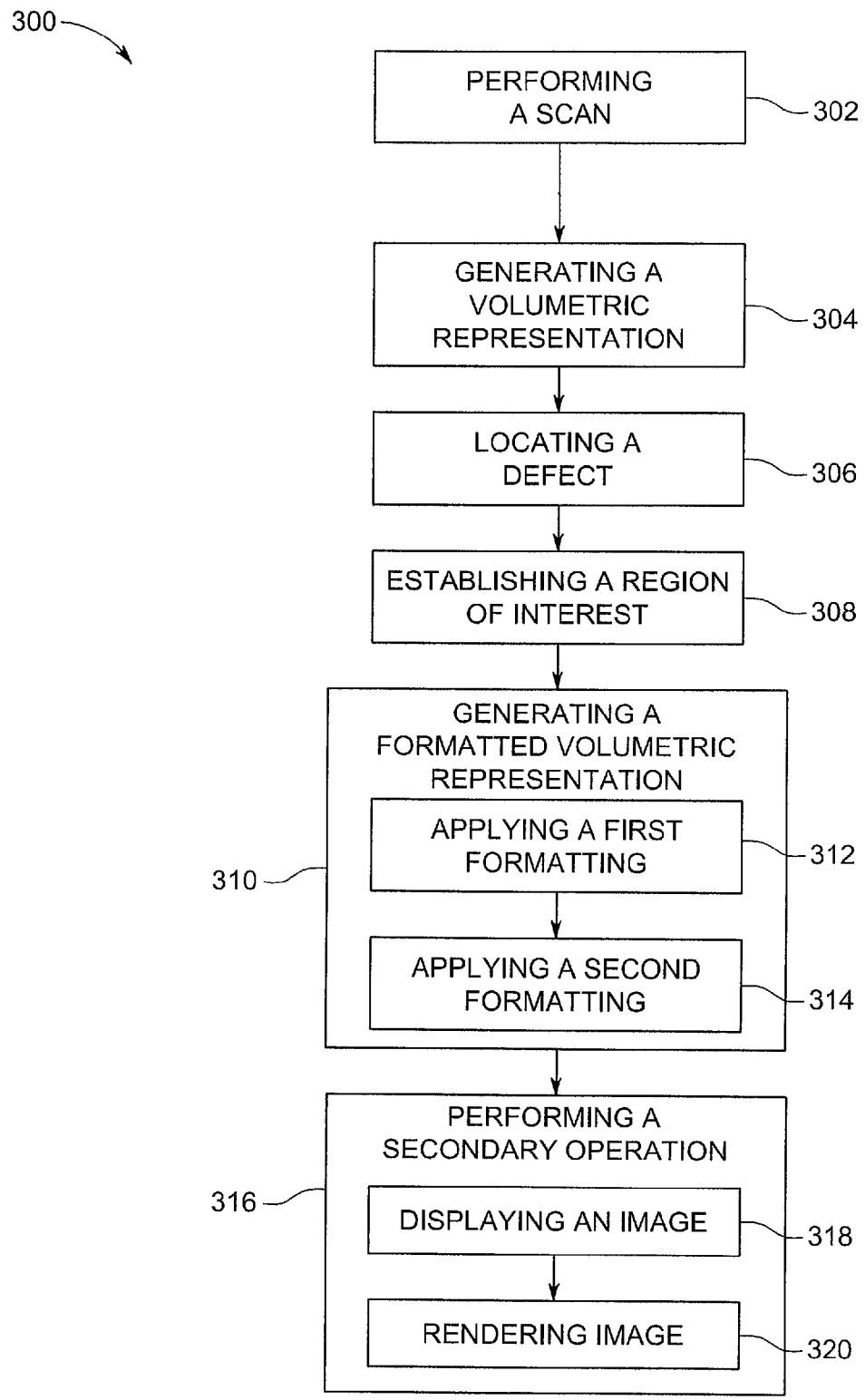
FIG. 3 depicts a flow diagram of an exemplary embodiment of a method for reducing the amount of data associated with a volumetric representation such as the volumetric representation of FIG. 2.

FIG. 3 illustrates a flow diagram of one exemplary embodiment of a method 300 to reduce the overall amount of data associated with non-destructive testing. Embodiments of the method 300 may take the form of executable instructions that cause certain elements (e.g., a CT scanner) of a testing system to operate. These instructions can reside on certain machine readable medium and/or computer program products such as, but not limited to, an electronic, magnetic, optical, electromagnetic, infrared, or semiconductor system, apparatus, or device, or any suitable combination thereof.

The method 300 includes, at block 302, performing a scan (e.g., a computed tomography (CT) scan) of a part-under-inspection (e.g., part 100 (FIG. 1)). The method 300 also includes, at block 304, generating a volumetric representation and, at block 306, locating a defect in the volumetric representation. The method 300 further includes, at block 308, establishing a region of interest around the defect and, at block 310, generating a formatted volumetric representation. The method 300 can comprise, at block 312, applying a first format to data corresponding to data inside the region of interest and, at block 314, applying a second format to data corresponding to data outside of the region of interest. The method 300 may also comprise, at block 316, performing a secondary operation such as, at block 318, displaying an image of the part-under-inspection on a display screen. The method 300 may further include, at block 320, rendering the image on the display using the reference volumetric representation.

The location of defects (e.g., defects 204 (FIG. 2)) may correspond to areas of the part-under-inspection where such defects are or are likely to be found. The locations may be proximate certain features of the part under inspection, e.g., a joint, fillet, hole (bore or aperture), and/or radius. In one example, the locations are pre-defined and, consequently, particular data of the volumetric representation of the part-under-inspection may become the focus of the method 300 over other data. In other examples, the method 300 may include steps or instructions that are useful to analyze all of the data of the volumetric representation and to identify the defects from that analysis. This analysis may, for example, identify anomalies and abnormalities in the data that are consistent with a type of defect.

The region of interest separates the data respecting the volumetric representation. The region of interest may define a hypothetical boundary that distinguishes particular pieces of data from others. The method 300 may, for example, implement this hypothetical boundary as part of data processing tasks, in which parameters (e.g., size and shape) for the region of interest identify the data in proximity to data respecting the defect discussed above.

In one embodiment, the method 300 may receive inputs from the end user that define the amount of data that the region of interest is to include. These inputs may define the parameters for the region of interest. In one example, the end user may select the parameters through a graphical user interface ("GUI") or other interactive tool. In other examples, certain executable instructions (e.g., software and/or firmware) may define (and/or automatedly define) such parameters. Criteria for selection of these parameters may include the type of defect and the nature of the part-under-inspection. In still other examples, a combination of end user input and automated definition may establish the parameters of the region of interest.

The region of interest may include data for only the defect, for a volume about the defect, and/or for other portions of the volumetric representation for use in inspection and analysis of the part-under-inspection. Data found inside the region of interest may be data that is retained for transfer, while data found outside of the region of interest may not be transferred or, in some cases, may be deleted altogether. In one embodiment, the region of interest dictates the type or level of formatting to which the data respecting the volumetric representation is subject. Formatting can take many forms, and in one example formatting in general defines changes to data by way of a data compression algorithm which compresses at least a portion of the data. Different types of data compression and algorithms for compressing data may improve the transfer of the data by, in one example, effectively reducing the total amount of data respecting the volumetric representation. Exemplary levels of data compression can vary as desired to facilitate this transfer but still maintain sufficient integrity of the data for useful analysis of the part-under-inspection. Data that is retained can be used, for example, to reject the part, to see if the defect under inspection criteria and/or passes such criteria, and to associate with the retained data certain information pertaining to the part under inspection, e.g., rate of failure in the field.

The first format and the second format may represent a level of data compression. In one example, the level of data compression for the first format is lower relative to the level for the second format. Exemplary data compression algorithms can include lossless and lossy compression methods, although the inventors understand that a wide variety of compression techniques are available to reduce the amount of data associated with the volumetric representation 200. In one embodiment, the formatted volumetric representation may result from application of each of the first format and the second format so the formatted volumetric representation comprises less data than the volumetric representation of the part-under-inspection.

Secondary operations can include image display as well as various other analytical tools such as finite element analysis ("FEA") tools. In one embodiment, the end user can view an image of the part-under-inspection via a workstation (with display screen). The workstation can render the image using data respecting the formatted volumetric representation. The resulting image may include data for each of the formatted volumetric representation and a reference volumetric representation. The reference volumetric representation, is useful for implementation in systems in which many of the same or substantially identical parts are to be inspected. In one example, the reference volumetric representation is generated from a sample of a part-under-inspection. This sample has features consistent with the myriad of parts-under-inspection and may provide additional details of the part-under-inspection that are not found in the formatted volumetric representation. The sample may be scanned and the data for the resulting reference volumetric representation can reside locally at the workstation so as to be retrieved, e.g., during rendering of the image. The inventors contemplate embodiments of the method 300 in which the reference volumetric representation provides the general outline of the part-under-inspection. The method 300 can integrate the formatted volumetric representation, which may provide the areas about the defect in high detail, with the reference volumetric representation to render the image for the end user.

Figure 4:
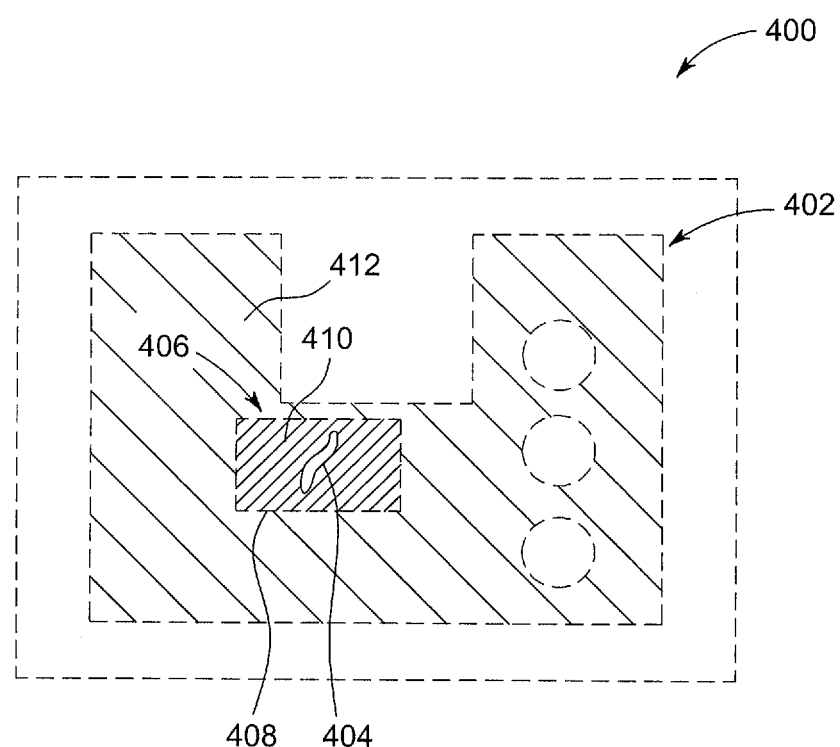
FIG. 4 depicts an example of an image that may result from the method of FIG. 3.

FIG. 4 illustrates a schematic drawing of an exemplary image 400 that may result from implementation of the method 300 discussed above. The image 400 is a two-dimensional view of a part 402 (e.g., the part of FIG. 1). The part 402 is shown with a defect 404 and a region of interest 406 in surrounding relation to the defect 404. The region of interest 406 comprises a boundary 408 that separates a first area 410 of the part 402 inside of the region of interest 406 from a second area 412 of the part 402 outside of the region of interest 406.

In one embodiment, the level of detail of the image 400 in the first area 410 is greater that the level of detail in the second area 412. This distinction may result from differences between the formatting associated with each of the formatted volumetric representation and the reference volumetric representation. For example, as discussed above, the formatted volumetric data comprises data that is selected and retained so as to provide a clear representation of the defect 404 as well as the area surrounding the defect 404 and defined by the region of interest (e.g., the region of interest 406). The reference volumetric representation, on the other hand, may comprise data that only provides essential features of the part 402 that give context to the viewer. These features may include only the general outline and/or shape of the part 402 (as evidenced by the dashed line) and/or other features of the part 402 that permit effective rendering of the image 400.

The boundary 408 defines a shape for the region of interest 406. As discussed above, parameters and features of the shape can be selected and/or assigned through the use of a user interface or other interactive diagnostic tool (e.g., a software application). The boundary 408 can also delineate between the level(s) of compression that the testing system applies to the data. This change may cause variations in the level of detail that is visible in the image 400. For example, the first area 410 may have more detail relative to the second area 412 because of the difference in the level of compression that the testing system applies to the data associated therewith.

Figure 5:
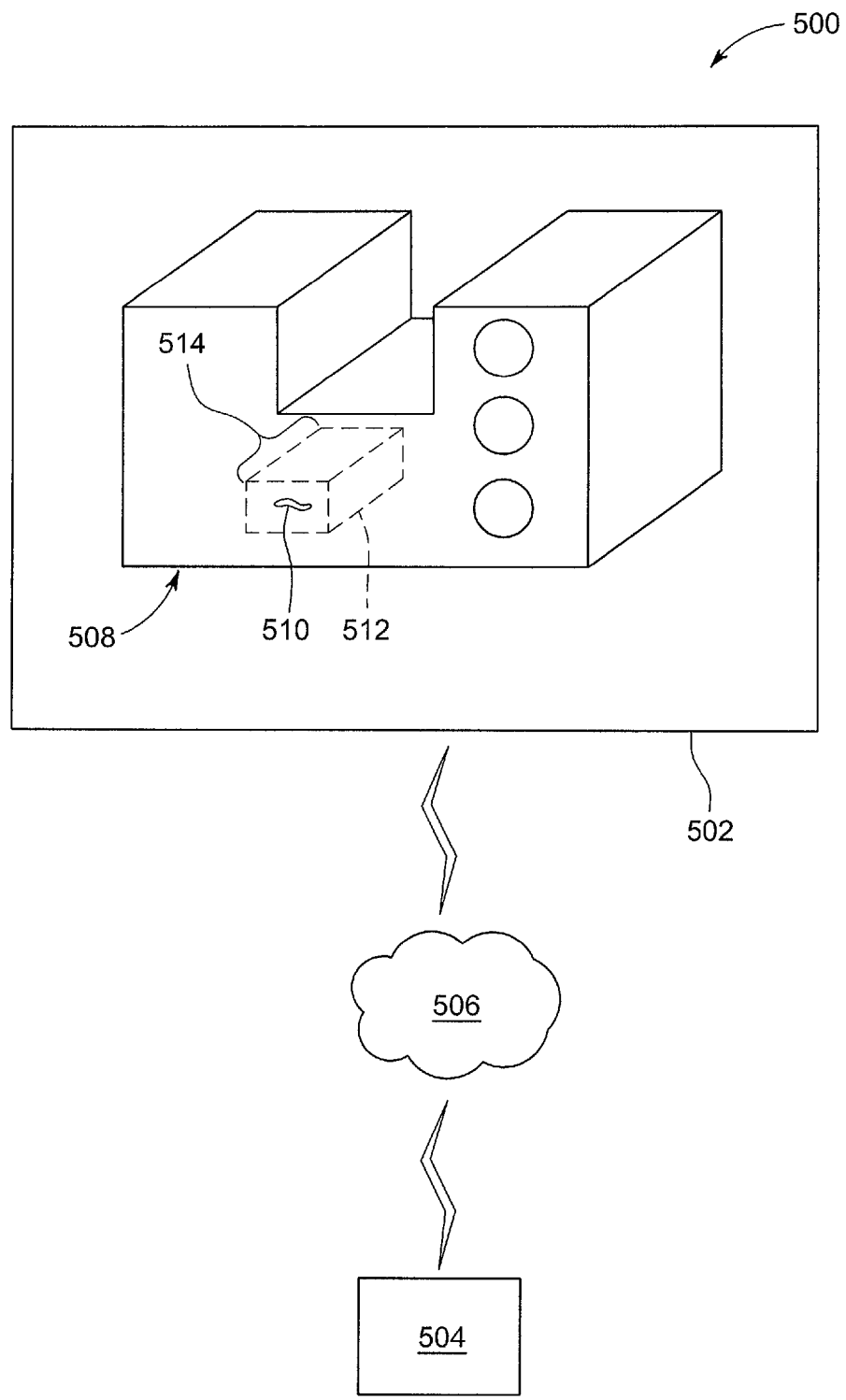
FIG. 5 depicts an exemplary embodiment of a non-destructive testing system that can implement the method of FIG. 3.

FIG. 5 illustrates an exemplary embodiment of a testing system 500 that can be used for non-destructive testing and inspection in various manufacturing environments (e.g., casting, molding, welding, etc.) Embodiments of the testing system 500 can comprise a scanner device 502 such as a computed tomography (CT) scanner, a data storage device 504, and a network 506, which communicatively couples the scanner device 502 and the data storage device 504. In one embodiment, the scanner device 502 can generate a volumetric representation 508 that is representative of, e.g., the part of FIG. 1. The volumetric representation 508 comprises a defect 510 and a region of interest 512. The region of interest 512 has a form factor 514 with a geometry that may encompass at least a portion of the defect 510. In the present example, the geometry is that of a rectangular volume, however, the geometry can take a variety of configurations.

The testing system 500 can communicate or transfer the data across the network 506. Communication may be wired, wireless, or by other means known in the art. The inventors likewise contemplate that cloud and cloud-based computing may provide adequate data transfer, storage, and retrieval options for implementation in connection with the testing system 500. In one example, data transfer may entail download and upload functions that facilitate movement of data between the scanner device 502 and remotely-located servers and/or databases that constitute the data storage device 504. By reducing, eliminating, and/or compressing the data as discussed above, the testing system 500 may alleviate issues and minimize the requirements on the testing system 500 that relatively large amounts of data may impose.

Figure 6:
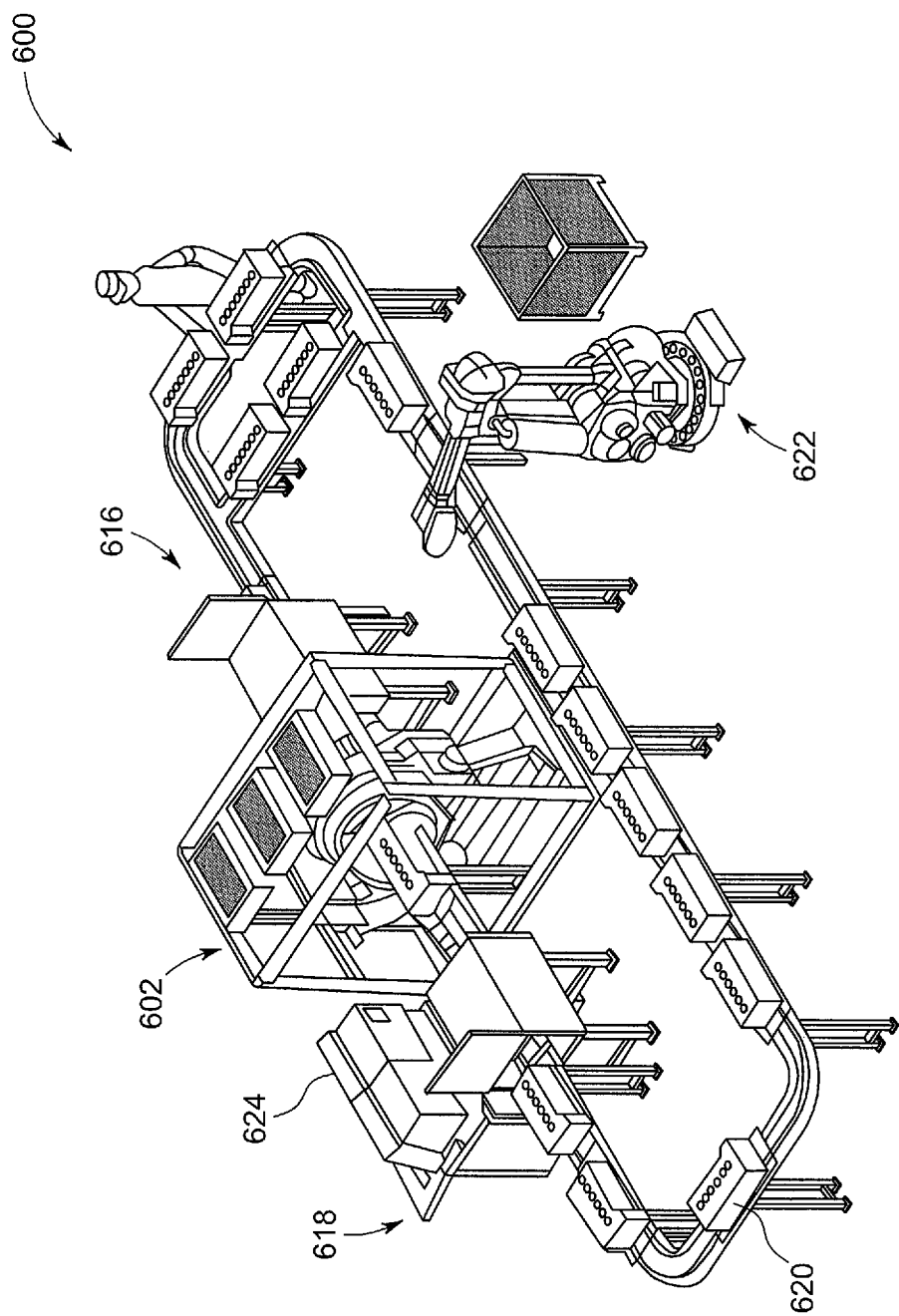
FIG. 6 depicts an exemplary embodiment of a production line that comprises a non-destructive testing system such as the non-destructive testing system of FIG. 5.

FIG. 6 provides additional details of another exemplary embodiment of a testing system 600. While like numerals are used to identify like elements as between the testing system 500 (FIG. 5) and the testing system 600 (FIG. 6), some elements have been removed for clarity and to focus the discussion that follows below. The testing system 600 comprises a scanner device 602. However, the data storage device and the network are not shown, but are applicable to the testing system 600 in the manner in which this disclosure describes them above.

The testing system 600 also comprises a conveyance device 616 and a control unit 618, which controls one or more of the scanner device 602 and the conveyance device 616. Located on the conveyance device 616 are various parts-under-inspection 620 such as molded or cast parts that manufacturing facilities may produce en mass. The testing system 600 also comprises a robotic manipulator 622 and one or more workstations 624, such as computer monitors and displays.

The conveyance device 616 can comprise a conveyor system or other configuration of components that can translate the parts-under-inspection 620 into and through the scanner device 602. These systems may integrate with existing manufacturing infrastructure found as part of a production or fabrication line. This configuration permits the continued or substantially continuous generation of data in the form of, e.g., volumetric representations, that are useful for quality review.

The control unit 618 may comprise various computing devices such as micro-controllers, data and micro processors, and the like. These devices can provide signals to the scanner device 602, the conveyance device 616, and the robotic manipulator 622. These signals may coordinate operation and, in one example, permit gathering of data from the volumetric representation. While the control unit 618 can provide analysis tools (e.g., software and hardware), the workstations 624 may likewise equip the testing system 600 with relevant operation capacity to monitor and analyze the data and information that the scanner device 602 provides. In one embodiment, the workstations 624 can include displays such as LCD displays that permit the end user to interact with the testing system as well as the data that the testing system gathers.

In view of the foregoing, the inventors propose configurations and methodologies that can increase the rate of exchange of data generated by a CT scanner. These configurations may reduce the amount of data that must transfer such as to archive or store the data on a data storage device. Data reduction can also improve the rate at which data is retrieved. Such improvements are helpful when, for example, a end user is located at a workstation remote from a data storage device and wishes to inspect a part-under-inspection on a display screen.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A testing system, comprising:
    a scanner device, wherein the scanner device comprises a computed tomography (CT) scanner; and
    a control unit coupled to the scanner device, the control unit operatively configured to generate one or more control signals to which the scanner device responds to generate a volumetric representation of a part-under-inspection,
    wherein the control unit is further configured to locate a region of interest comprising a defect in the volumetric representation and a volume immediately proximate the defect in the volumetric representation and to generate a formatted volumetric representation having less data than the volumetric representation, generating the formatted volumetric representation comprising deleting data found outside the region of interest in the volumetric representation.

2. A testing system according to claim 1, further comprising a conveyance device that is configured to transport the part-under-inspection to the scanner device.

3. A testing system according to claim 1, further comprising a data storage device, wherein the control unit is further configured to transfer data respecting the formatted volumetric representation to the data storage device.

4. A testing system according to claim 3, wherein the data storage device is remote from the control unit.

5. A testing system according to claim 3, wherein the control unit is further configured to establish the region of interest around the defect and to compress data outside of the region of interest.

6. A testing system according to claim 1, further comprising a workstation, wherein the workstation is configured to render an image of the part-under-inspection, and wherein the image comprises the formatted volumetric representation and a reference volumetric representation that provides peripheral details of the part-under-inspection.

7. A testing system according to claim 1, wherein the control unit is integrated into the scanner device.

8. A method for reducing data in a non-destructive testing system, said method comprising the steps of:
    performing, by a processor, a scan of a part-under-inspection;
    generating a volumetric representation from the scan;
    identifying, by the processor, a defect in the volumetric representation;
    establishing a region of interest around the defect in the volumetric representation and a volume immediately proximate the defect; and
    generating a formatted volumetric representation having less data than the volumetric representation, generating the formatted volumetric representation comprising deleting data found outside the region of interest in the volumetric representation.

9. The method of claim 8, further comprising the step of formatting data corresponding to each of the data inside the region of interest and outside the region of interest.

10. The method of claim 9, further comprising the step of applying a first format to data corresponding to data inside the region of interest.

11. The method of claim 10, further comprising the step of applying a second format to data corresponding to data outside the region of interest.

12. The method according to claim 11, wherein the first format is different from the second format.

13. The method of claim 8, further comprising the step of compressing data outside the region of interest.

14. The method of claim 13, further comprising the step of compressing each of the data inside and data outside of the region of interest.

15. The method of claim 8, further comprising the steps of:
    generating a reference volumetric representation; and
    rendering an image of the part-under-inspection using the formatted volumetric representation and the reference volumetric representation.

16. The method of claim 15, further comprising the step of formatting the reference volumetric representation so as to have less data than the volumetric representation.

17. The method of claim 8, wherein the scan utilizes a computed tomography (CT) scanner.

18. The method of claim 8, further comprising the step of receiving an input respecting parameters for the region of interest.

* * * * *